United States Patent [19]

Turconi et al.

[11] Patent Number: 5,106,851
[45] Date of Patent: Apr. 21, 1992

[54] BENZOFUSED-N-CONTAINING HETEROCYCLE DERIVATIVES

[75] Inventors: Marco Turconi, Voghera; Rosamarie Micheletti, Milan; Giovanni B. Schiavi, Asola; Arturo Donetti; Angelo Sagrada, both of Milan, all of Italy; Henri N. Doods, Warthausen, Fed. Rep. of Germany

[73] Assignee: Istituto de Angeli S.p.A., Milan, Italy

[21] Appl. No.: 474,187

[22] Filed: Feb. 2, 1990

[30] Foreign Application Priority Data

Feb. 6, 1989 [IT] Italy .................. 19316 A/89

[51] Int. Cl.$^5$ .................. A61K 31/505; C07D 239/96; C07D 521/00
[52] U.S. Cl. .................................. 514/259; 544/284; 544/285; 544/286
[58] Field of Search .................. 544/285, 286, 284; 514/259

[56] References Cited

U.S. PATENT DOCUMENTS 4,599,336 7/1986 Carson et al. .................. 544/286
4,849,513 7/1989 Glazer .................. 544/285

OTHER PUBLICATIONS

"Chemical Abstracts", vol. 98, 1983, col. 98:53926m.

*Primary Examiner*—C. Warren Ivy
*Assistant Examiner*—James H. Turnipseed
*Attorney, Agent, or Firm*—David E. Frankhouser; Alan R. Stempel; Mary-Ellen M. Timbers

[57] ABSTRACT

Compounds of the formula (I)

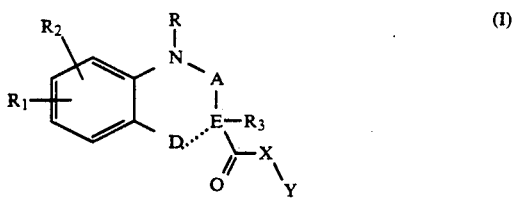

wherein
R represents H or $C_{1-6}$ alkyl;
$R_1$ and $R_2$ represent H, halogen, $C_{1-6}$ alkyl, $C_{1-6}$ alkoxy, $C_{1-6}$ alkythio, $C_{1-6}$ alkoxycarbonyl, carboxyl, hydroxy, nitro, cyano, optionally $C_{1-4}$ alkyl mono- or disubstituted carbamoyl, optionally $C_{1-4}$ alkyl mono- or disubstituted amino, $C_{1-6}$ acylamino, $C_{1-4}$ alkoxy carbonylamino, $C_{1-6}$ alkylsulphynyl, $C_{1-6}$ alkylsulphonyl or $C_{1-6}$ acyl;
$R_3$ represents H, $C_{1-6}$ alkyl, aryl or aralkyl, or it may be absent;
A represents CO or C=S;
E represents nitrogen;
D represents CO or $CR_4R_5$ when the E—D bond is single, or D is C—R when the D—E bond is double, in which $R_4$ represents H, $C_{1-6}$ alkyl, aryl, aralkyl, hydroxy or $C_{1-4}$ alkoxy and $R_5$ represents H;
X represents oxygen or N—R, or it is absent;
Y represents a basic group selected from:

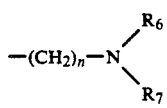

a)

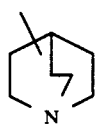

b)

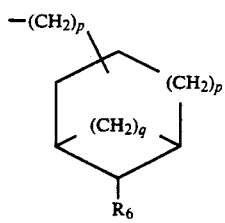

c)

in which n is 2 or 3; p is 0 or 1 at the same time or not; q is 0,2 or 3; $R_6$ and $R_7$ may be at the same time or not, H, $C_{1-4}$ alkyl, aralkyl or, when $R_7$ is H or $C_{1-4}$ alkyl, $R_6$ may be —$CR_8$=N—R in which $R_8$ represents H, $C_{1-4}$ alkyl or amino.

6 Claims, No Drawings

BENZOFUSED-N-CONTAINING HETEROCYCLE DERIVATIVES

The present invention relates to novel pharmacologically active benzofused-N-containing heterocycle derivatives, to the process for their preparation and to the pharmaceutical compositions containing them. The new compounds are muscarinic receptors blocking agents and are useful for the treatment of the gastro intestinal and respiratory tract disorders.

It is known that administration of muscarinic receptor blocking agents gives rise to a number of pharmacological effects like decreased gastrointestinal motility, inhibition of acid secretion, bronchodilation, dry mouth, mydriasis, urinary retention, decreased sweating, tachycardia. Furthermore, antimuscarinic agents with tertiary amine structures may give rise to central effects owing to their penetration across blood-brain barrier. The lack of selectivity among these actions makes it difficult to address therapy in one specific indication and this prompted chemical modification of these agents. A major improvement in this sense was achieved with the discovery of Pirenzepine which is able to bind with high affinity to the muscarinic receptors ($M_1$ type) located in neuronal tissues (brain, ganglia), in the enteric nervous system and in lung tissues; nowadays Pirenzepine is therapeutically used as an antisecretory and antiulcer agent [R. Hammer et al.—Nature 283 90 (1980), N. J. M. Birdsall et al.—Scand. J. Gastroenterol: 15 (Suppl. 66) 1 (1980)], moreover its use in the treatment of bronchoconstriction has been claimed (Pat. Appln. WO 8608 278). The receptors with low affinity to Pirenzepine ($M_2$ type), present mainly but not exclusively, in effector organs were further subdivided according to the different abilities of selected antagonists in inhibiting the muscarinic responses in tissue preparations such as guinea pig longitudinal ileum and guinea pig paced left atria [R. B. Barlow et. al.—British J. Pharmacol. 89 837 (1986); R. Micheletti et al.—J. Pharmacol. Exp. Ther. 241 628 (1987); R. B. Barlow et al.—British J. Pharmacol. 58 631 (1976)].

The compound AF-DX-116 (11-2-{[2-(diethylamino)methyl-1-piperidinyl]acetyl}-5,11-dihydro-6H-pyrido (2,3-b)(1,4)benzodiazepin-6-one) may be considered the prototype of cardioselective compounds, whereas 4-DAMP (4-diphenylacetoxy-N-methylpiperidine methobromide) is the prototype of smooth muscle selective compounds.

We have now synthetized, and this is an object of the present invention, a novel class of benzofused-N-containing heterocycle derivatives which show affinity and selectivity for the $M_1$ receptors, in comparison with $M_2$ receptors, far superior to Pirenzepine as measured by receptor binding studies.

Moreover, unlike Pirenzepine, these novel compounds are able to antagonize potently and selectively the functional muscarinic responses in selected smooth muscles as shown in in vitro and in in vivo studies. The novel compounds may therefore be used in the treatment of gastrointestinal disorders such as peptic ulcer disease, irritable bowel syndrome, spastic constipation, cardiospasm, pylorospasm without concomitant effects on heart rate and without other atropine-like side-effects.

The compounds object of the present invention, may be also used in the treatment of obstructive acute and chronic spastic disorders of the respiratory tract, such as bronchoconstriction, chronic bronchitis, emphysema and asthma without atropine-like side-effects, particularly on the heart.

Furthermore they may be used in the treatment of the spasms of the urinary and biliary tracts and in the treatment of urinary incontinence.

According to the present invention we provide compounds of general formula (I)

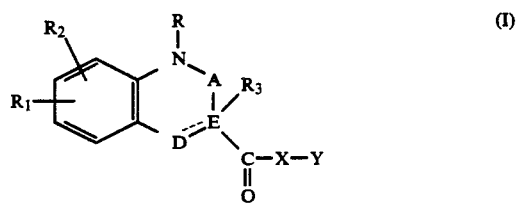

wherein

R represents H or $C_{1-6}$ alkyl;

$R_1$ and $R_2$ represent H, halogen, $C_{1-6}$ alkyl, $C_{1-6}$ alkoxy, $C_{1-6}$ alkylthio, $C_{1-6}$ alkoxycarbonyl, carboxyl, hydroxy, nitro, cyano, optionally $C_{1-4}$ alkyl mono- or disubstituted carbamoyl, optionally $C_{1-4}$ alkyl mono- or disubstituted amino, $C_{1-6}$ acylamino, $C_{1-4}$ alkoxy carbonylamino, $C_{1-6}$ alkylsulphynyl, $C_{1-6}$ alkylsulphonyl, $C_{1-6}$ acyl;

$R_3$ represents H, $C_{1-6}$ alkyl, aryl, aralkyl or it may be absent;

A represents CO, C=S, S→O or

E represents nitrogen when $R_3$ is absent and the E—D bond is single, or it is carbon;

D represents CO, $CH_2$—$CH_2$,

when the E—D bond is single, or D is C—R when the D—E bond is double, in which $R_4$ represents H, $C_{1-6}$ alkyl, aryl, aralkyl, hydroxy, $C_{1-4}$ alkoxy and $R_5$ represents H;

X represents oxygen, N—R or it is absent;

Y represents a basic group selected from:

a)

b)

-continued

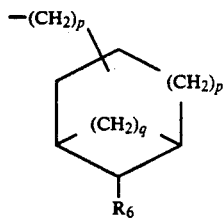

c)

in which n is 2 or 3; p is 0 or 1 at the same time or not; q is 0, 2 or 3; $R_6$ and $R_7$ may be at the same time or not H, $C_{1-4}$ alkyl, aralkyl or, when $R_7$ is H or $C_{1-4}$ alkyl, $R_6$ may be

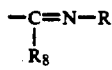

in which $R_8$ represents H, $C_{1-4}$ alkyl or amino.

For pharmaceutical use, the compounds of general formula (I) may be used as such or in the form of tautomers thereof, and the invention further includes physiologically acceptable acid addition salts of the compounds of formula (I) and tautomers thereof. The term "acid addition salt" includes salts either with inorganic or organic acids. Physiologically acceptable organic acids which may be used in salt formation include, for example, maleic, citric, tartaric, fumaric, methanesulphonic and benzenesulphonic acid; suitable inorganic acids include hydrochloric, hydrobromic, nitric and sulphuric acid.

Physiologically acceptable salts include also quaternary derivatives of compounds of formula (I) obtained by reaction of the above compounds with compounds of formula $R_9$—Q wherein $R_9$ is a linear or branched $C_{1-6}$ alkyl or $C_{3-7}$ cycloalkyl—$(CH_2)_m$, m is 1 or 2, and Q is a leaving group such as halogen, p-toluensulphonate or mesylate. Preferred $R_9$ groups are methyl, ethyl, isopropyl, cyclopropylmethyl. Physiologically acceptable salts include also internal salts of compounds of formula (I) such as N-oxides. The compounds of formula (I) and their physiologically acceptable salts may also exist as physiologically acceptable solvates such as hydrates. All such forms are included within the invention.

It should be understood that the invention further includes the tautomers of the amidino derivatives of formula (I) wherein $R_6$ is a group of formula

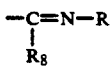

in which $R_8$ and R are as herein before defined. The present invention includes within its scope these tautomeric forms both in terms of compounds and manufacturing processes.

Some of the compounds of formula (I) according to the present invention contain chiral or prochiral centres and thus may exist in different stereoisomeric forms including enantiomers of (+) and (−) type or mixtures of them. The present invention includes in its scope both the individual isomers and the mixtures thereof.

It should be understood that, when mixtures of optical isomers are present, they may be separated according to the classical resolution methods based on different physico-chemical properties, e.g. by fractional crystallization of the acid addition salts with a suitable optically active acid or by the chromatographic separation with a suitable mixture of solvents.

In preferred embodiments of the present invention, the term "halogen" generally denotes fluorine, chlorine, bromine or iodine and when Y in formula (I) corresponds with formula (b), Y represents a 3- or 4-linked 1-azabicyclo[2.2.2]octane. When Y represents formula (c), Y represents 3- or 4-linked piperidine, 3-linked-8-azabicyclo[3.2.1]octane or 3-linked 9-azabicyclo[3.3.1]nonane.

It should also be understood that, in the compounds of formula (I) the azabicyclic moieties of group Y may be endo- or exo-substituted. Compounds of formula (I) containing the pure endo-or exo-moieties may be prepared starting from the appropriate precursors or by separating mixtures of endo- or exo-isomers not stereospecifically synthetized by conventional methods such as e.g. chromatography.

Preferred compounds according to the present invention include those wherein Y is endo-8-methyl-8-azabicyclo[3.2.1]oct-3-yl and endo-9-methy-9-azabicyclo[3.2.1]oct-3-yl, B is nitrogen, R is hydrogen, $R_3$ is absent, the B—D bond is single and $R_1$, $R_2$, D, X are as hereinbefore defined. Such compounds generally have a good affinity for $M_1$ receptor subtypes and for ileal receptors.

The compounds of general formula (I) may be prepared according to different alternatives of methods. According to a further feature of the invention we provide a process for the preparation of compounds of formula (I) as described hereinbefore in which:

a) a compound of general formula (II)

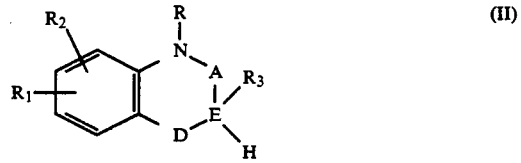

(II)

wherein R, $R_1$, $R_2$, $R_3$, A, E, D are as hereinbefore defined, is reacted with a compound of formula (III)

(III)

wherein X and Y are as hereinbefore defined and Q is a leaving group such as halogen, $C_{1-4}$ alkoxy, $C_{1-4}$ alkanoyloxy, $C_{1-4}$ alkoxycarbonyloxy, preferably chlorine, methoxy, ethoxy. The compound of formula (II) must be previously activated to a reactive compound of general formula (IV)

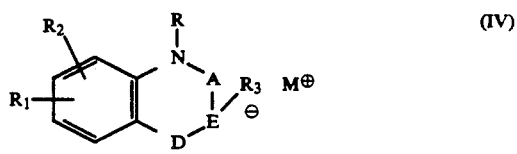

(IV)

wherein M is a metal atom such as lithium, sodium or potassium by an activating agent such as n-butyllithium, lithiumdiisopropylamide (LDA), sodium hydride, sodium amide, potassium hydride, potassium t-butilate, preferably n-butyllithium, LDA or sodium hydride at −70° C. or at room temperature in an aprotic solvent such as tetrahydrofurane or dimethylformamide and then the reaction is run in the same solvent at a temperature ranging from −70° C. to 60° C., preferably between −50° C. and room temperature, according to the selected solvent.

b) When it is desired to prepare compounds of formula (I) wherein B is carbon and X is oxygen or N—R, a compound of formula (V)

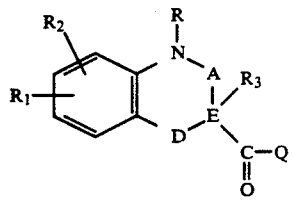 (V)

wherein R, $R_1$, $R_2$, $R_3$, A, D are as above defined and Q is hydroxyl or any group as hereinbefore defined, is reacted with a compound of formula (VI)

H—X—Y (VI)

wherein X and Y are as hereinbefore defined. In the case that Q is halogen preferably chlorine, the reaction is carried out in an inert aprotic solvent such as tetrahydrofurane, methylene dichloride, ethylacetate, acetonitrile, acetone, benzene, optionally in the presence of an organic or inorganic acid acceptor such as triethylamine, pyridine, 1,8-diazabicyclo[5.4.0]undec-7-ene (DBU), sodium or potassium carbonate. The reaction may be carried out at a temperature ranging from −10° C. to the boiling point of the selected solvent, preferably at room temperature. In certain instances compounds of formula (VI) wherein X is oxygen may be reacted as reactive derivatives such as salts with alkali metals, preferably lithium or sodium salts. In the case that Q is a $C_{1-4}$ alkoxy preferably methoxy or ethoxy, the reaction is generally carried out in an inert solvent such as benzene, toluene, heptane capable of azeotropically removing the formed alcohol QOH, optionally in the presence of a catalyst such as sodium metal. Reaction temperatures are preferably at the boiling point of the selected solvent. In the case that Q is hydroxyl the reaction is generally carried out in an inert aprotic solvent such as tetrahydrofurane, methylene dichloride, dimethylformamide in the presence of a condensing agent such as dicyclohexylcarbodiimide or carbonyldiimidazole optionally in the presence of a catalyst such as pyridine, 4-dimethylaminopyridine or DBU. Compounds of formula (VI) wherein X is oxygen may be reacted as reactive derivatives as hereinbefore defined. The reaction may be generally performed between 0° C. and 80° C., preferably at room temperature. When Q is a $C_{1-4}$ alkanoyloxy or $C_{1-4}$ alkoxycarbonyloxy, preferably propanoyloxy or propoxycarbonyloxy the reaction may be generally carried out in the same manner as if Q were a halogen.

c) When it is desired to prepare compounds of formula (I) wherein B is nitrogen, R is hydrogen and $R_3$ is absent, a compound of general formula (VII)

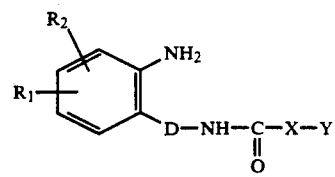 (VII)

wherein $R_1$, $R_2$, D, X and Y are as hereinbefore defined, is reacted with compounds of general formula (VIII)

$$Q_1-\underset{\underset{O}{\|}}{C}-Q_2 \quad \text{(VIII)}$$

wherein $Q_1$ and $Q_2$, identical or different from each other, are leaving groups such as halogen, optionally halogenated $C_{1-4}$ alkoxy, imidazolyl, optionally substituted phenoxy, preferably chlorine, ethoxy, phenoxy, trichloromethoxy or imidazolyl. The reaction may be generally carried out in an aprotic solvent such as tetrahydrofurane, methylene dichloride, chloroform, acetone, acetonitrile, optionally in the presence of an acid acceptor such as triethylamine, pyridine, sodium or potassium carbonate at a temperature temperature. If between 20° C. and 100° C., preferably at room temperature. If desired the same compounds may be obtained by reacting the intermediate of general formula (IX), which is formed during the above reaction and then isolated

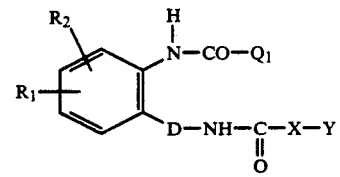 (IX)

in which $R_1$, D, X, Y, $R_2$ and $Q_1$ are as hereinbefore defined, in solvents such as ethanol, tetrahydrofurane, dimethylformamide, benzene, toluene in the presence of an organic or inorganic base such as triethylamine, trimethylamine, DBU, sodium hydroxide, sodium hydride, potassium t-butylate, preferably triethylamine or sodium hydroxide, at a temperature between room temperature and the boiling point of the selected solvent, preferably between room temperature and 60° C.

The compound of general formula (VII) used as starting material in the above process may be prepared by reducing a compound of general formula (X)

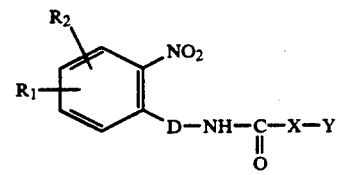 (X)

wherein $R_1$, D, X, Y and $R_2$ are as hereinbefore defined. The reduction is generally carried out in a solvent such as water, methanol, ethanol, tetrahydrofurane or mixtures of them in an hydrogen atmosphere in the presence of a suitable catalyst such as palladium on carbon, platinum dioxide, Raney-Nickel, preferably palladium or platinum at a temperature between 20° C. and 60° C.

and at a pressure between 1 and 20 atm., preferably at 20° C. and atmospheric pressure.

The compounds of formula (X), wherein $R_1$, $R_2$, D, X and Y are as hereinbefore defined, may be prepared by reacting compounds of general formula (XI)

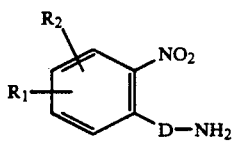
(XI)

with compounds of general formula (XII)

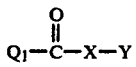
(XII)

wherein $Q_1$ is hereinbefore defined. The reaction is carried out in an inert or basic solvent such as methylene dichloride, tetrahydrofurane, chloroform, pyridine or a mixtures of them at a temperature between 0° C. and 80° C., preferably between 20° C. and 50° C.

In an additional option the compounds of formula (X) may be prepared by reacting a compound of general formula (XIII)

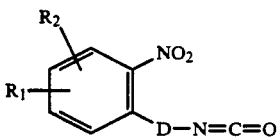
(XIII)

in which D is as above defined, with a compound of formula (VI). The reaction is carried out in an inert solvent such as tetrahydrofurane, methylene dichloride, chloroform, ethylacetate, acetonitrile, acetone or a mixture of them, preferably methylene dichloride, at a temperature ranging from 0° to 60° C., preferably at 20° C.

Compounds of general formula (XIII) may be used as such or prepared "in situ" from the re-arrangement of suitable carboxylic acid derivatives of general formula (XIV)

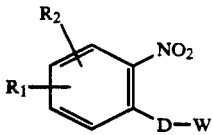
(XIV)

wherein D is as hereinbefore defined and W is $CONH_2$, $CONHNH_2$ or $CON_3$. The reaction is carried out according to conventional methods related to the Hofmann and Curtis re-arrangements reactions.

It has to be understood that compounds of general formula (I) containing a group R, $R_1$, $R_2$, $R_4$, $R_5$, $R_6$ and $R_7$ which may give rise to another group R, $R_1$, $R_2$, $R_4$, $R_5$, $R_6$, $R_7$ are also new useful intermediates. Some examples of such conversions, which obviously are not exhaustive of all the possibilities are:

1. A halogen group may be converted into a hydrogen atom by hydrogenolysis.
2. A carbamoyl group may be converted into a cyano group by dehydration.
3. A secondary amido group may be converted into a tertiary amido group by alkylation in the presence of an activator such as sodium hydride.
4. A methylenic group may be converted into —CH—OH group by oxidation.
5. An amino group may be converted into an amidino group by reaction with suitable reactives such as esters of imidic acids, cyanamide, N-nitro-S-methyl-isothiourea, S-methyl isothiouronium sulphate.
6. A secondary amino group may be converted into a tertiary amino group by alkylation.
7. An amino benzyl derivative may be debenzylated by hydrogenation.

These conversions are well known to anyone skilled in the art. The compounds of general formula (I), prepared according to the process as above described, may optionally be converted with organic or inorganic acids into the corresponding physiologically compatible acid addition salts, for example, by conventional methods such as by reacting the compounds as bases with a solution of the corresponding acid in a suitable solvent. Particularly preferred acids include, for example, hydrochloric, hydrobromic, citric, tartaric, benzenesulphonic acid.

Particularly preferred compounds, according to the present invention, are the following:

1,4-dihydro-2(H)-2-oxo-3-quinazolinecarboxylic acid-(endo-8-methyl-8-azabicyclo[3.2.1]oct-3-yl), ester. (Compound 16)

N-(endo-8-methyl-8-azabicyclo[3.2.1]oct-3-yl)-1,4-dihydro-2(H)-2-oxo-quinazoline-3-carboxamide. (Compound 23)

7-chloro-1,4-dihydro-2(H)-2-oxo-3-quinazolinecarboxylic acid-(endo-8-methyl-8-azabicyclo[3.2.1]oct-3-yl), ester. (Compound 25)

1,4-dihydro-6-fluoro-2(H)-2-oxo-3-quinazoline carboxylic acid-(endo-8-methyl-8-azabicyclo[3.2.1]oct-3-yl), ester. (Compound 26)

1,4-dihydro-4-hydroxy-2(H)-2-oxo-3-quinazolinecarboxylic acid-(endo-8-methyl-8-azabicyclo[3.2.1]oct-3-yl), ester. (Compound 49)

As already mentioned hereinbefore the new compounds of formula (I), according to the present invention, have interesting pharmacological properties owing to their ability to antagonize the physiological muscarinic effects in warm blooded animals. Therefore the new compounds are therapeutically useful in the prevention or in the treatment of disorders wherein muscarinic receptors are involved, particularly for disorders related to excessive acid secretion, altered bowel motility and obstructive spastic disorders of the respiratory tract without showing any effect on heart rate.

The following tests show that the compounds according to the invention have favourable characteristics in this respect.

PHARMACOLOGY

Antimuscarinic activity and selectivity

Antimuscarinic activity and selectivity were examined in in vitro by receptor binding studies in two tissues endowed with $M_1$ and $M_2$ muscarinic receptors (cerebral cortex, heart), in functional studies in isolated guinea pig ileum and guinea pig paced left atria and in in vivo functional tests on bronchi and heart of the anaesthetized guinea pig.

Receptor binding studies in vitro

Muscarinic $M_1$ activity was determined by studying the displacement of $^3$H-pirenzepine from cerebral cortex homogenate according to the procedure reported below: The cerebral cortex donors were male CD-COOBBS rats, 220–250 g body weight. The homogenization process was carried out in a Potter-Evelhjem apparatus in the presence of $Na^+/Mg^{++}$ HEPES buffer; pH 7.4 (100 mM NaCl, 10 mM $MgCl_2$, 20 mM HEPES); by filtering the suspension through two layers of cheesecloth. Binding curves for the under study compounds were derived indirectly from competition experiments against 0.5 nM $^3$H-pirenzepine labelling the muscarinic receptors of the cerebral cortex. 1 ml of the homogenate was incubated for 45 min at 30° C. in the presence of a maker ligand and different concentration of the cold ligand, conditions under which equilibrium was reached as determined by appropriate association experiments. The incubation was terminated by centrifugation (12,000 rpm for 3 min) at room temperature using an Eppendorf microcentrifuge. The resultant pellet was washed twice with 1.5 ml saline to remove the free radioactivity and it was allowed to dry. The tips of the tubes containing the pellet were cut off and 200 μl of tissue solubilizer (Lumasolve, Lumac) were added and left to stand overnight. Radioactivity was then counted after addition of 4 ml of liquid scintillation mixture (Dimilume/Toluene 1+10 v:v, Packard).

Assays were carried out in triplicate or quadruplicate and the non-specific binding was defined as the radioactivity bound or entrapped in the pellet when the incubation medium contained 1 μM atropine sulphate. Non-specific binding averaged less than 30%. $K_D$ values (dissociation constants) were obtained by non-linear regression analysis on the basis of one binding site model with TOPFIT-pharmacokinetic programme package (G. Heinzel "Pharmacokinetics During Drug Development: Data Analysis and Evaluation Techniques" Eds. G. Bolzer and J. M. Van Rossum; p. 207, G. Fisher, New York, 1982) after correction for the radioligand occupancy shift according to the equation: $K_D = IC_{50}/1 + {^*C}/{^*K_D}$, where $^*C$ and $^*K_D$ represent the concentration and the dissociation constants of the radioligand, used respectively. Muscarinic $M_2$ activity was examined by studing the displacement of $^3$H-NMS from total heart homogenate according to a procedure identical to the one already described hereinbefore for the muscarinic $M_1$ activity.

Functional studies in vitro

Guinea pig ileum

A 2 cm section of terminal ileum was prepared according to Edinburgh Staff —1974— "Pharmacological Experiments on Isolated Preparations" 2nd Edition, Edinburgh: Churchill Livingstone, suspended in Tyrode solution, and contracted with cumulative concentrations of bethanechol (conc. range 0.3–10 μM, $EC_{50}$ 1.5 μM). Responses were recorded isotonically. $K_b$ values were calculated according to Arunlakshana and Shild (British Journal of Pharmacology 14, 48–54, 1959).

Guinea pig left atria

The tissues were mounted in the Ewen's solution (millimolar: NaCl, 131.6; KCl, 5.6; $CaCl_2$, 2.16; $NaHCO_3$, 24.9; $NaH_2PO_4$, 1.03; glucose, 11; and sucrose, 13) at 32° C. and stimulated through platinum electrodes by squarewave pulses (2 msec, 3 Hz, 100% above threshold voltage, delivered by a Grass S 48 stimulator). Inotropic activity was recorded isometrically (Statham transducer, Battaglia Rangoni ESO 300 recorder). Cumulative concentrations of bethanecol (1–30 μM) were used to induce a negative inotropic effect. $K_b$ values were estimated as above described.

The results of the tests are set in the following table:

| Compound | Receptor binding studies $K_D$ (nM) | | Functional studies $K_b$ (nM) | |
|---|---|---|---|---|
| | $M_1$ (cortex) | $M_2$ (heart) | ileum | heart |
| 16 | 1 | 133 | 1.5 | 122 |
| 23 | 1 | 60 | 0.6 | 22 |
| 26 | 3 | 400 | 4.5 | 250 |
| 25 | 7 | 1470 | 16.0 | 2200 |
| 49 | 2 | 250 | 1.0 | 75 |

In vivo activity at Muscarinic receptors in the bronchi and heart of the anaesthetized guinea pig Guinea pigs of either sex (550–600 g) were anaesthetized with urethane (1.4 g/kg, i.p.). A jugular vein was cannulated for injection of drugs. Heparin (200 I.U./kg) was injected i.v. A cannula was placed in the trachea and the animals were artificially respirated with oxygenated room air by means of a positive pressure pump (Braun-Melsungen) with a rate of 80 strokes/min. A side arm of the tracheal cannula was connected to a water manometer of 10 cm height. The respiratory volume was adjusted so that the maximal intratracheal pressure during inspiration just attained to a pressure of 10 cm water.

Excepts for some modifications, the effects of the drugs on bronchial tone was measured according to the method described by Konzett and Rössler (1940). The bronchoconstriction-evoked volume of respiratory gas mixture (overflow) passing through the water manometer was measured by means of a FLEISCH tube pneumotachometer (Model 0000) connected to a SP 2040 D differential pressure transducer (HSE). Registration was performed on a IFD recording device. Before the experiment, the trachea was clamped during a short period of time in order to obtain the maximum possible degree of bronchoconstriction for calibration.

A cannula was placed in the left common carotid artery and arterial blood pressure was measured via a Bell and Howell 4-327 I pressure transducer connected to an IFD recording device. Cardiac frequency was measured by a ratemeter, triggered by the arterial pulsewave.

The drugs to be tested were injected via the jugular vein and 5 min later bronchial resistence (%) and the decrease in cardiac frequence (beats/min) to acetylcholine (50 μg/kg i.v. and i.a.) was measured. Dose response curves were constructed by plotting the percent inhibition of bronchoconstriction and bradycardia against the logarithm of the dose (mol/kg) of the drugs to be tested. Results were presented as mean values as reported in the following table:

| | in vivo studies ($-\log ED_{50}$) | |
|---|---|---|
| Compound | bronchi | heart |
| 16 | 8.1 | 6.0 |

According to a further feature of the present invention there are provided pharmaceutical compositions comprising as active ingredient at least one compound of formula (I), as hereinbefore defined, or a physiologically acceptable acid addition salt thereof in association with one or more pharmaceutical carriers, diluents or excipients. For pharmaceutical administration the compounds of general formula (I) and their physiologically acceptable acid addition salts may be incorporated into the conventional pharmaceutical preparations in either solid or liquid form. The compositions may, for example, be presented in a form suitable for oral, rectal or parenteral administration. Preferred forms include, for example, capsules, tablets, coated tablets, ampoules, suppositories and oral drops.

The active ingredient may be incorporated in excipients or carriers conventionally used in pharmaceutical compositions such as, for example, talc, arabic gum, lactose, gelatine, magnesium stearate, corn starch, aqueous or non-aqueous vehicles, polyvinylpirrolidone, semisynthetic glicerides of fatty acids, sorbitol, propylene glycol, citric acid, sodium citrate.

The compositions are advantageously formulated in dosage units, each dosage unit being adapted to supply a single dose of the active ingredient. Each dosage unit may conveniently contain from 0.01 mg to 100 mg and preferably from 0.05 mg to 50 mg.

The following examples illustrate some of the new compounds according to the present invention; these examples are not to be in any way limitative of the scope of the invention itself:

EXAMPLE 1

β-[(4-chloro-2-nitro)phenyl]-α-ethoxycarbonyl-propanoic acid, ethyl ester

Diethylmalonate (3.5 ml) was dropped into a suspension of 80% sodium hydride in oil (0.69 g) in dry tetrahydrofuran (10 ml) at room temperature under stirring. Stirring was continued for 1 hour, then a solution of 4-chloro-2-nitrobenzylbromide (2.9 g) in tetrahydrofuran (10 ml) was added. The reaction mixture was stirred for an additional hour, then water and ethylacetate were added. The organic layer was separated and dried over $MgSO_4$. After evaporation of the solvent an oil was left, which was distilled, thus affording 1.5 g of the title compound. B.p. 157°-160° C. (0.5 mmHg).

Analogously, starting from the appropriate compounds, the following intermediates were prepared:

β-(2-nitrophenyl)-α-ethoxycarbonyl-α-phenyl-propanoic acid, ethyl ester. B.p. 180°-182° C. (0.1 mmHg).

β-(2-nitrophenyl)-α-ethoxycarbonyl-α-methyl-propanoic acid, ethyl ester. B.p. 145°-146° C. (0.2 mmHg).

EXAMPLE 2

7-chloro-1,2,3,4-tetrahydro-2-oxo-3-quinoline carboxylic acid, ethyl ester

A mixture of β-[(4-chloro-2-nitro)phenyl]-α-ethoxycarbonylpropanoic acid, ethyl ester (1.8 g), iron powder (0.9 g) and acetic acid (20 ml) was stirred at 80° C. for 3 hours. After cooling, the solvent was evaporated under vacuum and the residue was taken up into ethylacetate and water. The organic layer was separated and dried over $MgSO_4$ and after evaporation of the solvent 0.95 g of the pure title compound were obtained. M.p. 182°-184° C.

Similarly the following intermediates were prepared:
3-methyl-1,2,3,4-tetrahydro-2-oxo-3-quinoline carboxylic acid, ethyl ester. M.p. 110°-111° C.
3-phenyl-1,2,3,4-tetrahydro-2-oxo-3-quinoline carboxylic acid, ethyl ester. M.p. 157°-158° C.

EXAMPLE 3

4-phenyl-1,2,3,4-tetrahydro-2-oxo-3-quinoline carboxylic acid, ethyl ester 80 g of concentrated sulphuric acid were dropped into a suspension of 4-phenyl-1,2,3,4-tetrahydro-2-oxo-3-quinoline carbonitrile (15 g) in ethanol (70 ml) and the whole was heated to reflux for 1 hour. After cooling the reaction mixture was poured onto ice and the aqueous layer was extracted with ethylacetate. After the usual workup 20 g of raw material were obtained. After purification by flash chromatography technique (Silicagel eluted with methylene dichloride/ethylacetate 85:15) 8.3 g of title compound were obtained. M.p. 178°-180° C.

EXAMPLE 4

7-chloro-1,2,3,4-tetrahydro-2-oxo-3-quinoline carboxylic acid 7-chloro-1,2,3,4-tetrahydro-2-oxo-3-quinoline carboxylic acid, ethyl ester (1.35 g) was dissolved into a solution of potassium hydroxide (0.76 g) in ethyl alcohol (15 ml) at room temperature under stirring. A solid soon separated and was recovered by filtration after 2 hours. The solid was dissolved into cold water and hydrochloric acid was added until precipitation of a white solid took place. The title acid was recovered by filtration and after drying 1.0 g were obtained. M.p. 158°-160° C.

Similarly also the following compounds were prepared:
3-phenyl-1,2,3,4-tetrahydro-2-oxo-3-quinoline carboxylic acid. M.p. 169°-170° C.
3-methyl-1,2,3,4-tetrahydro-2-oxo-3-quinoline carboxylic acid. M.p. 164°-165° C.
3-ethyl-1,2,3,4-tetrahydro-2-oxo-3-quinoline carboxylic acid. M.p. 169°-170° C.
4-phenyl-1,2,3,4-tetrahydro-2-oxo-3-quinoline carboxylic acid. M.p. 175°-177° C.

EXAMPLE 5

(+)-3-methyl-1,2,3,4-tetrahydro-2-oxo-3-quinoline carboxylic acid

A hot solution of (±)-3-methyl-1,2,3,4-tetrahydro-2-oxo-3-quinoline carboxylic acid (20 g) and L(−)-α-methylbenzylamine (12.43 ml) in ethanol (4 lt) was allowed to cool to room temperature and to stay for 48 hrs. The white solid that separated (9 g) was collected by filtration. M.p. 173°-174° C. 3 g of this solid were dissolved in water, cooled to 0° C. and acidified. The title compound (0.75 g) was obtained by filtration and was free from the other isomer as judged by TLC over Chiralplate[R] (Macherey-Nagel), eluent: water/methanol/acetonitrile 50:50:10 in comparison with the racemic compound. M.p. 139°-141° C.

$[\alpha]^{25}_D + 37.19°$ (c 2.0, EtOH).

EXAMPLE 6

(−)-3-methyl-1,2,3,4-tetrahydro-2-oxo-3-quinoline carboxylic acid

Similarly to example 5, starting from 26 g of racemic acid, 16.2 ml of R(+)-α-methylbenzylamine and 4.5 lt of ethanol, 9.5 g of a white solid were obtained. M.p. 175°–176° C. From 3 g of this compound 1.4 g of pure title compound were obtained. M.p. 139°–141° C. $[\alpha]^{25}_D$ −38.98° (c 2.0, EtOH).

EXAMPLE 7

N-(5-fluoro-2-nitrophenyl)methyl-phthalimide

A solution of 5-fluoro-2-nitro-benzylbromide (6.2 g) in dimethylformamide (20 ml) was dropped into a stirred suspension of potassium phthalimide (4.9 g) in the same solvent (40 ml). The mixture was heated under stirring to 90° C. for 2 hours, then cooled and diluted with water. The title compound (7.2 g) was recovered by filtration. M.p. 198°–200° C.

Similarly the following compounds can be prepared:
N-(5-cyano-2-nitrophenyl)methyl-phthalimide.
N-(5-carbamoyl-2-nitrophenyl)methyl-phthalimide. M.p. 265°–267° C.
N-(2-methyl-6-nitrophenyl)methyl-phthalimide, mixed with N-(2-methyl-3-nitrophenyl)methyl-phthalimide. M.p. 100°–124° C.
N-(2-hydroxy-6-nitrophenyl)methyl-phthalimide. M.p. 243°–246° C.
N-(4-fluoro-2-nitrophenyl)methyl-phthalimide. M.p. 176°–178° C.

EXAMPLE 8

5-fluoro-2-nitrobenzylamine

85% Hydrazine hydrate (1.67 ml) was added to a suspension of N-(5-fluoro-2-nitrophenyl)methyl-phthalimide (7.1 g) in ethanol (90 ml). The reaction mixture was heated to reflux for 3 hours, then cooled to 40° C. Hydrochloric acid was added and stirring was continued at that temperature for a further hour; then the solvent was removed under vacuum. The residue was taken up in water and the solid which separated was discarded. The mother liquors were treated with 10% sodium hydroxide and extracted with diethyl ether. After evaporation of the solvent 3.5 g of title compound were obtained as a reddish oil.

IR (nujol) $\nu$ (cm$^{-1}$): 3400, 3300, 1620, 1580, 1515.

Similarly the following compounds can be obtained:
5-cyano-2-nitrobenzylamine
5-carbamoyl-2-nitrobenzylamine. M.p. 143°–145° C.
2-hydroxy-6-nitrobenzylamine. Hydrochloride salt. M.p. 254°–255° C.
2-methyl-6-nitrobenzylamine, mixed with 2-methyl-3-nitrobenzylamine, oil.
4-fluoro-2-nitrobenzylamine, oil.

EXAMPLE 9

N-(2-nitrobenzyl)-(endo-8-methyl-8-azabicyclo[3.2.1]oct-3-yl)carbamate 2-nitrobenzylamine (13.9 g) and triethylamine (10.17 g) were dissolved in methylene dichloride (60 ml) and the resulting solution was dropped into a suspension of endo-8-methyl-8-azabicyclo[3.2.1]oct-3-yl chloroformate, hydrochloride (21.93 g) in the same solvent (200 ml) under stirring at room temperature. The yellow solution was stirred for further 30 min, then it was concentrated to dryness. The residue was taken up in diluted hydrochloric acid, washed with a little ethylacetate, treated with diluted sodium hydroxide and extracted into ethylacetate. After evaporation of the solvent and crystallization from ethanol 26.1 g of the title compound were obtained. M.p. 143°–145° C.

Similarly the following compounds can be obtained from the appropriate starting compounds:
N-(5-methyl-2-nitrobenzyl)-(endo-8-methyl-8-azabicyclo[3.2.1]oct-3-yl)carbamate. Oil IR (nujol) $\nu$ (cm$^{-1}$): 3320, 1710, 1610, 1590, 1520.
N-(5-methoxy-2-nitrobenzyl)-(endo-8-methyl-8-azabicyclo[3.2.1]oct-3-yl)carbamate. M.p. 216°–218° C.
N-(5-chloro-2-nitrobenzyl)-(endo-8-methyl-8-azabicyclo[3.2.1]oct-3-yl)carbamate. Hydrochloride. M.p. 208°–210° C.
N-(2-nitrobenzyl)-1-methylpiperidine-4-carboxamide. M.p. 126°–128° C.
N-(2-nitrobenzyl)-1-methylpiperidine-4-acetamide. M.p. 93°–95° C.
N-(2-nitrobenzyl)-(1-azabicyclo[2.2.2]oct-3-yl), carbamate. M.p. 112°–114° C.
N-(2-nitrobenzyl)-(endo-8-benzyl-8-azabicyclo[3.2.1[oct-3-yl), carbamate. M.p. 89°–91° C.
N-(2-nitrobenzyl)-(endo-8-ethyl-8-azabicyclo[3.2.1]oct-3-yl), carbamate. M.p. 130°–132° C.
N-(2-nitrobenzyl)-(endo-9-methyl-9-azabicyclo[3.3.1]nonan-3-yl), carbamate. Oil IR (nujol) $\nu$ (cm$^{-1}$): 3320, 1720–1690, 1610, 1580, 1520.
N-(4-chloro-2-nitrobenzyl)-(endo-8-methyl-8-azabicyclo[3.2.1]oct-3-yl), carbamate. Hydrochloride. M.p. 204°–206° C.
N-(5-fluoro-2-nitrobenzyl)-(endo-8-methyl-8-azabicyclo[3.2.1]oct-3-yl), carbamate. M.p. 115°–117° C.
N-[2-(2-nitrophenyl)ethyl]-(endo-8-methyl-8-azabicyclo[3.2.1]oct-3-yl), carbamate. Hydrochloride. M.p. 198°–201° C.
N-(2-nitrobenzyl)-1-methylpyrrolidin-3-yl, carbamate. Oil. IR (nujol) $\nu$ (cm$^{-1}$): 3320, 1710–1690, 1610, 1580, 1520.
N-(5-cyano-2-nitrobenzyl)-(endo-8-methyl-8-azabicyclo[3.2.1]oct-3-yl), carbamate.
N-(5-carbamoyl-2-nitrobenzyl)-(endo-8-methyl-8-azabicyclo[3.2.1]oct-3-yl), carbamate. M.p. 185°–186° C.
N-(4-fluoro-2-nitrobenzyl)-(endo-8-methyl-8-azabicyclo[3.2.1]oct-3-yl), carbamate. M.p. 120°–122° C.
N-(2-methyl-6-nitrobenzyl)-(endo-8-methyl-8-azabicyclo[3.2.1]oct-3-yl), carbamate, mixed with N-(2-methyl-3-nitrobenzyl)-(endo-8-methyl-8-azabicyclo[3.2.1]oct-3-yl) carbamate. Hydrochloride salt. M.p. 233°–235° C.
N-(2-hydroxy-6-nitrobenzyl)-(endo-8-methyl-8-azabicyclo[3.2.1]oct-3-yl), carbamate. M.p. 68°–70° C.
N-(4,6-dichloro-2-nitrobenzyl)-(endo-8-methyl-8-azabicyclo[3.2.1]oct-3-yl), carbamate.
N-(6-chloro-2-nitrobenzyl)-(endo-8-methyl-8-azabicyclo[3.2.1]oct-3-yl), carbamate. Hydrochloride. M.p. 265°–267° C.
N-(2-amino-α-methylbenzyl)-(endo-8-methyl-8-azabicyclo[3.2.1]oct-3-yl), carbamate. M.p. 134°–136° C.
N-(2-nitrobenzyl)-(endo-8-cyclopropylmethyl-8-azabicyclo[3.2.1]oct-3-yl), carbamate. M.p. 93°–94° C.

N-(2-nitrobenzyl)-(endo-8-isopropyl-8-azabicyclo[3.2.-1]oct-3-yl), carbamate. M.p. 110°-112° C.

EXAMPLE 10

N-(2-nitrobenzyl)-N'-(endo-8-methyl-8-azabicyclo[3.2.-1]oct-3-yl), urea

A solution of (2-nitrophenyl)acetylchloride (1.0 g) in acetone (3 ml) was dropped into a solution of sodium azide (0.39 g) in water (5 ml) at room temperature under stirring. After 30 min. a solid separated, which was then recovered after dilution with water and filtration. The same solid was dissolved in chloroform (20 ml); the solution was dried over $MgSO_4$, filtered and refluxed for 30 min. To this solution 3-α-amino-8-methyl-8-azabicyclo[3.2.1]octane (0.55 g) was added at 5° C. After an hour the resulting solution was concentrated to dryness and the pure title compound (0.4 g) was obtained after flash chromatography on Silicagel (eluent: methylene dichloride/methanol/32% ammonium hydroxyde 80:20:2). M.p. 191°-193° C.

Similarly, starting from 2-nitrobenzoylisocyanate, the following compound was prepared:
N-(2-nitrobenzoyl)-N'-(endo-8-methyl-8-azabicyclo[3.2.1]oct-3-yl), urea. M.p. 217°-220° C.

EXAMPLE 11

N-(2-aminobenzyl)-(endo-8-methyl-8-azabicyclo[3.2.-1]oct-3-yl), carbamate

A solution of N-(2-nitrobenzyl)-(endo-8-methyl-8-azabicyclo[3.2.1]oct-3-yl), carbamate (26 g) in ethanol (250 ml) was hydrogenated at room temperature and atmosphere pressure in the presence of 10% Pd/C (1.3 g) to give, after the usual workup, 20.65 g of the title compound. M.p. 130°-132° C.

Similarly, employing the proper catalyst, the following compounds can be obtained:
N-(2-amino-5-methylbenzyl)-(endo-8-methyl-8-azabicyclo[3.2.1]oct-3-yl), carbamate. M.p. 128°-131° C.
N-(2-amino-5-methoxybenzyl)-(endo-8-methyl-8-azabicyclo[3.2.1]oct-3-yl), carbamate. M.p. 115°-118° C.
N-(2-aminobenzyl)-1-methylpiperidin-4-yl-carboxamide. M.p. 128°-130° C.
N-(2-aminobenzyl)-1-methylpiperidin-4-yl-acetamide. Oil. IR (nujol) ν (cm$^{-1}$): 1660, 1630, 1550.
N-(2-aminobenzyl)-(1-azabicyclo[2.2.2]oct-3-yl), carbamate. M.p. 125°-128° C.
N-(2-aminobenzyl)-(endo-8-benzyl-8-azabicyclo[3.2.-1]oct-3-yl), carbamate. M.p. 129°−132° C.
N-(2-aminobenzyl)-(endo-8-ethyl-8-azabicyclo[3.2.-1]oct-3-yl), carbamate. Oil.
N-(2-aminobenzyl)-(endo-9-methyl-9-azabicyclo[3.3.1]nonan-3-yl), carbamate. M.p. 105°-106° C.
N-[2-(2-aminophenyl)ethyl]-(endo-8-methyl-8-azabicyclo[3.2.1]oct-3-yl), carbamate. M.p. 145°-147° C.
N-(2-aminobenzyl)-1-methylpyrrolidin-3-yl, carbamate. M.p. 129°-131° C.
N-(2-amino-5-carbamoylbenzyl)-(endo-8-methyl-8-azabicyclo[3.2.1]oct-3-yl), carbamate. M.p. 74°-75° C.
N-(2-amino-6-methylbenzyl)-(endo-8-methyl-8-azabicyclo[3.2.1]oct-3-yl) carbamate, mixed with N-(3-amino-2-methylbenzyl)-(endo-8-methyl-8-azabicyclo[3.2.1]oct-3-yl)carbamate. M.p. 72°-74° C.
N-(2-amino-6-hydroxybenzyl)-(endo-8-methyl-8-azabicyclo[3.2.1]oct-3-yl), carbamate. M.p. 186°-187° C.
N-(2-aminobenzyl)-N'-(endo-8-methyl-8-azabicyclo[3.2.1]oct-3-yl), urea. M.p. 176°-178° C.
N-(2-aminobenzyl)-N'-(endo-8-methyl-8-azabicyclo[3.2.1]oct-3-yl), urea, hydrochloride. M.p. 239°-240° C.
N-(2-aminobenzyl)-(endo-8-ciclopropylmethyl-8-azabicyclo[3.2.1]oct-3-yl), carbamate. M.p. 131°-132° C.
N-(2-aminobenzyl)-(endo-8-isopropyl-8-azabicyclo[3.2.1]oct-3-yl), carbamate, oil.

EXAMPLE 12

N-(2-amino-5-chlorobenzyl)-(endo-8-methyl-8-azabicyclo[3.2.1]oct-3-yl), carbamate A solution of N-(5-chloro-2-nitrobenzyl)-(endo-8-methyl-8-azabicyclo[3.2.1]oct-3-yl), carbamate hydrochloride (2.0 g) in water (40 ml) was heated to reflux for 30 min in the presence of iron powder (0.87 g) and of a catalytic amount of $FeCl_3$. The cooled reaction mixture was poured into ice, treated with 10% sodium hydroxyde, extracted into methylene dichloride and dried over $MgSO_4$. Upon evaporation of the solvent 1.43 g of the title compound were obtained. M.p. 156°-158° C.

Similarly the following compounds can be obtained:
N-(2-amino-4-chlorobenzyl)-(endo-8-methyl-8-azabicyclo[3.2.1]oct-3-yl), carbamate. M.p. 160°-162° C.
N-(2-amino-5-fluorobenzyl)-(endo-8-methyl-8-azabicyclo[3.2.1]oct-3-yl), carbamate. M.p. 148°-150° C.
N-(2-amino-5-cyanobenzyl)-(endo-8-methyl-8-azabicyclo[3.2.1]oct-3-yl), carbamate.
N-(2-amino-4-fluorobenzyl)-(endo-8-methyl-8-azabicyclo[3.2.1]oct-3-yl), carbamate. M.p. 145°-146° C.
N-(2-amino-4,6-dichlorobenzyl)-(endo-8-methyl-8-azabicyclo[3.2.1]oct-3-yl), carbamate.
N-(2-amino-6-chlorobenzyl)-(endo-8-methyl-8-azabicyclo[3.2.1]oct-3-yl), carbamate. M.p. 165°-167° C.

EXAMPLE 13

1,2,3,4-Tetrahydro-2-oxo-3-quinoline carboxylic acid-(endo-8-methyl-8-azabicyclo[3.2.1]oct-3-yl), ester

Compound 1

Carbonyldiimidazole (2.54 g) was added to a solution of 1,2,3,4-tetrahydro-2-oxo-3-quinoline carboxylic acid in dry DMF (6 ml) and the whole was stirred at room temperature under nitrogen for 10 min. To this solution a solution of endo-8-methyl-8-azabicyclo[3.2.1]oct-an-3-ol (2.42 g) and sodium hydride (0.048 g) in the same solvent (6 ml) was added. Stirring was continued for 3 hrs, then acetic acid was added until neutrality. The solvent was removed under vacuum, the residue was taken up in diluted hydrochloric acid and washed with ethyl acetate. The aqueous layer was then treated with saturated $Na_2CO_3$ and the raw title compound extracted into methylene dichloride. 3.7 g of the pure title compound as maleic acid salt were obtained from ethylacetate. M.p. 195°-197° C.

Analysis $C_{18}H_{22}N_2O_3 \cdot C_4H_4O_4$: Found %: C 60.28; H 6.04; N 6.39. Calc. %: C 61.38; H 6.09; N 6.51.
Similarly the following compounds were obtained:

N-[2-(N',N'-diethylamino)ethyl]-1,2,3,4-tetrahydro-2-oxo-3-quinoline carboxamide

Compound 2

M.p. 121°-122° C.
Analysis $C_{16}H_{23}N_2O_3$: Found %: C 66.44; H 8.16; N 14.47. Calc. %: C 66.41; H 8.01; N 14.52.

1,2,3,4-tetrahydro-2-oxo-3-quinoline carboxylic acid-(1-methylpiperidin-4-yl) ester Compound 3

M.p. 154°–156° C.
Analysis $C_{16}H_{20}N_2O_3$: Found %: C 66.71; H 7.08; N 9.68. Calc. %: C 66.64; H 6.99; N 9.72.

1,2,3,4-tetrahydro-2-oxo-3-quinoline carboxylic acid-[2-(N,N-diethylamino)ethyl], ester Compound 4

M.p. 92°–93° C.
Analysis $C_{16}H_{22}N_2O_3$: Found %: C 66.25; H 7.63; N 9.61. Calc. %: C 66.18; H 7.64; N 9.63.

7-chloro-1,2,3,4-tetrahydro-2-oxo-3-quinoline carboxylic acid-(1-azabicyclo[2.2.2]oct-3-yl), ester Compound 5

Hydrochloride salt. M.p. 244°–246° C.
Analysis $C_{17}H_{19}ClN_2O_3$.HCl: Found %: C 54.71; H 5.37; N 7.45. Calc. %: C 55.08; H 5.42; N 7.54.

1,2,3,4-tetrahydro-2-oxo-3-quinoline carboxylic acid-(endo-7-methyl-7-azabicyclo[2.2.1]heptane), ester Compound 6

Hydrochloride salt. M.p. 97°–100° C. (lyophilized).
Analysis $C_{17}H_{20}N_2O_3$.HCl: Found %: C 59.81; H 6.29; N 8.12. Calc. %: C 60.26; H 6.28; N 8.32.

4-phenyl-1,2,3,4-tetrahydro-2-oxo-3-quinoline carboxylic acid-(1-azabicyclo[2.2.2]oct-3-yl), ester Compound 7

M.p. 204°–205° C.
Analysis $C_{23}H_{24}N_2O_3$: Found %: C 73.01; H 6.28; N 7.45. Calc. %: C 73.57; H 6.18; N 7.46.

EXAMPLE 14

3-methyl-1,2,3,4-tetrahydro-2-oxo-3-quinoline carboxylic acid-(endo-8-methyl-8-azabicyclo[3.2.1]oct-3-yl), ester Compound 8

3-methyl-1,2,3,4-tetrahydro-2-oxo-3-quinoline carboxylic acid (1.5 g) was dissolved in freshly distilled thionyl chloride (15 ml) and heated to 40° C. for one and a half hour. The halogenating agent was removed under vacuum with the aid of benzene. The acid chloride so obtained was dissolved in dry acetonitrile (CH₃CN) (30 ml) and dropped, under stirring at room temperature, into a solution of endo-8-methyl-8-azabicyclo[3.2.1]octan-3-ol (1.13 g) and triethylamine (0.96 g) in the same solvent (40 ml). Stirring was continued overnight then the reaction mixture was concentrated to dryness. The usual workup afforded 0.3 g of the title compound as a base, from which 0.35 g of the tartaric acid salt were obtained. M.p. 101°–102° C. (after lyophilization).
Analysis $C_{19}H_{24}N_2O_3.C_4H_6O_6$: Found %: C 57.03; H 6.34; N 5.75. Calc. %: C 57.73; H 6.32; N 5.86.

Similarly the following compounds were obtained:

3-methyl-1,2,3,4-tetrahydro-2-oxo-3-quinoline carboxylic acid-(1-azabicyclo[2.2.2]oct-3-yl), ester Compound 9

Tartaric acid salt. M.p. ≈70° C. (lyophilized).
Analysis $C_{18}H_{22}N_2O_3.C_4H_6O_6$ Found %: C 55.52; H 6.17; N 5.81. Calc. %: C 56.88; H 6.07; N 6.03.

3-methyl-1,2,3,4-tetrahydro-2-oxo-3-quinoline carboxylic acid-(1-methylpiperidin-3-yl), ester Compound 10

Tartaric acid salt. M.p. 98°–100° C. (lyophilized).
Analysis $C_{17}H_{22}N_2O_3.C_4H_6O_6$: Found %: C 54.93; H 6.15; N 6.03. Calc. %: C 55.74; H 6.24; N 6.19.

(+)-3-methyl-1,2,3,4-tetrahydro-2-oxo-3-quinoline carboxylic acid-(endo-8-methyl-8-azabicyclo[3.2.1]oct-3-yl), ester Compound 11

Hydrochloride salt. M.p. 228°–230° C.
Analysis $C_{19}H_{24}N_2O_3$.HCl: Found %: C 62.36; H 6.95; N 7.51. Calc. %: C 62.54; H 6.91; N 7.68.
$[\alpha]_D^{25}$ −21.29° C. (c 1.5, EtOH).

(−)-3-methyl-1,2,3,4-tetrahydro-2-oxo-3-quinoline carboxylic acid-(endo-8-methyl-8-azabicyclo[3.2.1]oct-3-yl), ester Compound 12

Hydrochloride salt. M.p. 228°–230° C.
Analysis $C_{19}H_{24}N_2O_3$.HCl: Found: C 62.15; H 6.97; N 7.55. Calc. %: C 62.54; H 6.91; N 7.68.
$[\alpha]_D^{25}$ −22.76° C. (c 1.5, EtOH).

1,2-dihydro-2-oxo-3-quinoline carboxylic acid-(endo-8-methyl-8-azabicyclo[3.2.1]oct-3-yl), ester Compound 13

Citric acid salt. M.p. 107°–110° C.
Analysis $C_{18}H_{20}N_2O_3.C_6H_8O_7$: Found %: C 56.83; H 5.56; N 5.38. Calc. %: C 57.14; H 5.59; N 5.55.

3-ethyl-1,2,3,4-tetrahydro-2-oxo-3-quinoline carboxylic acid-(endo-8-methyl-8-azabicyclo[3.2.1]oct-3-yl), ester Compound 14

Tartaric acid salt. M.p. 57°–59° C. (lyophilized).
Analysis $C_{20}H_{26}N_2O_3.C_4H_6O_6$: Found %: C 57.39; H 6.51; N 5.59. Calc. %: C 58.52; H 6.55; N 5.68.

3-phenyl-1,2,3,4-tetrahydro-2-oxo-3-quinoline carboxylic acid-(1-azabicyclo[2.2.2]oct-3-yl), ester Compound 15

M.p. 223°–224° C.
Analysis $C_{23}H_{24}N_2O_3$: Found %: C 73.18; H 6.45; N 7.41. Calc. %: C 73.38; H 6.43; N 7.44.

EXAMPLE 15

1,4-dihydro-2(H)-2-oxo-3-quinazoline carboxylic acid-(endo-8-methyl-8-azabicyclo[3.2.1]oct-3-yl), ester Compound 16

A solution of N-(2-nitrobenzyl)-(endo-8-methyl-8-azabicyclo[3.2.1]oct-3-yl) carbamate (30.4 g) and triethylamine (12.74 g) in methylene dichloride (0.5 lt) was added dropwise (2.5 hrs) into a cooled (3°÷6° C.) solution of trichloromethylchloroformate (22.86 g) in the same solvent (240 ml). The resulting solution was stirred for a further hour at room temperature, then water was added and the organic layer was discarded. The aqueous layer was treated with 10% sodium hydroxide and extracted into methylene dichloride. After drying, evaporation of the solvent left a raw material which was crystallized as the hydrochloride salt from ethanol. 30.3 g.

M.p. >260° C. Free base m.p. 175°-177° C.

Analysis $C_{17}H_{21}N_3O_3 \cdot HCl$: Found %: C 58.28; H 6.36; N 11.68. Calc. %: C 58.03; H 6.30; N 11.94.

MS (C.I.): 316 m/e [M+H]+.

Similarly the following compounds can be obtained:

1,4-dihydro-6-methyl-2(H)-2-oxo-3-quinazoline carboxylic acid-(endo-8-methyl-8-azabicyclo[3.2.1]oct-3-yl), ester Compound 17

Citric acid salt. M.p. 158°-160° C.

Analysis $C_{18}H_{23}N_3O_3 \cdot C_6H_8O_7$: Found %: C 54.72; H 6.02; N 7.90. Calc. %: C 55.27; H 5.99; N 8.05.

1,4-dihydro-6-methoxy-2(H)-2-oxo-3-quinazoline carboxylic acid-(endo-8-methyl-8-azabicyclo[3.2.1]oct-3-yl), ester Compound 18

Hydrochloride salt. M.p. >260° C.

Analysis $C_{18}H_{23}N_3O_4 \cdot HCl$: Found %: C 56.19; H 6.35; N 10.90. Calc. %: C 56.61; H 6.33; N 11.00.

6-chloro-1,4-dihydro-2(H)-2-oxo-3-quinazoline carboxylic acid-(endo-8-methyl-8-azabicyclo[3.2.1]oct-3-yl), ester Compound 19

Hydrochloride salt. M.p. >260° C.

Analysis $C_{17}H_{20}ClN_3O_3 \cdot HCl$: Found %: C 52.88; H 5.50; N 10.68. Calc. %: C 52.86; H 5.48; N 10.88.

3-[(1-methylpiperidin-4-yl)carbonyl]-1,4-dihydro-2(H)-quinazoline-2-one

Compound 20

Hydrochloride salt. M.p. 243°-245° C.

Analysis $C_{15}H_{19}N_3O_2 \cdot HCl$: Found %: C 57.64; H 6.51; N 13.57. Calc. %: C 58.16; H 6.51; N 13.56.

3-[2-(1-methylpiperidin-4-yl)acetyl]-1,4-dihydro-2(H)-quinazoline-2-one

Compound 21

M.p. 159°-161° C.

Analysis $C_{16}H_{21}N_3O_2$: Found %: C 66.68; H 7.39; N 14.64. Calc. %: C 66.87; H 7.37; N 14.62.

1,4-dihydro-2(H)-2-oxo-3-quinazoline carboxylic acid-(1-azabicyclo[2.2.2]oct-3-yl), ester Compound 22

Maleic acid salt. M.p. 115°-118° C.

Analysis $C_{16}H_{19}N_3O_3 \cdot C_4H_4O_4$: Found %: C 57.01; H 5.59; N 9.89. Calc. %: C 57.55; H 5.55; N 10.07.

N-(endo-8-methyl-8-azabicyclo[3.2.1]oct-3-yl)-1,4-dihydro-2(H)-2-oxo-3-quinazoline carboxamide Compound 23

Hydrochloride salt. M.p. >260° C.

Analysis $C_{17}H_{22}N_4O_2 \cdot HCl$: Found %: C 57.83; H 6.64; N 15.81. Calc. %: C 58.19; H 6.61; N 15.97.

1,4-dihydro-2(H)-2-oxo-3-quinazoline carboxylic acid-(endo-9-methyl-9-azabicyclo[3.3.1]non-3-yl), ester Compound 24

Hydrochloride salt. M.p. 220°-222° C.

Analysis $C_{18}H_{23}N_3O_3 \cdot HCl$: Found %: C 58.74; H 6.65; N 11.41. Calc. %: C 59.09; H 6.61; N 11.49.

7-chloro-1,4-dihydro-2(H)-2-oxo-3-quinazoline carboxylic acid-(endo-8-methyl-8-azabicyclo[3.2.1]oct-3-yl), ester Compound 25

Hydrochloride salt. M.p. >260° C.

Analysis $C_{17}H_{20}ClN_3O_3 \cdot HCl$ Found %: C 51.55; H 5.47; N 10.66. Calc. %: C 52.86; H 5.48; N 10.88.

1,4-dihydro-6-fluoro-2(H)-2-oxo-3-quinazoline carboxylic acid-(endo-8-methyl-8-azabicyclo[3.2.1]oct-3-yl), ester Compound 26

Hydrochloride salt. M.p. >260° C.

Analysis $C_{17}H_{20}FN_3O_3 \cdot HCl$: Found %: C 54.96; H 5.79; N 11.24. Calc. %: C 55.21; H 5.72; N 11.36.

1,4-dihydro-4-methyl-2(H)-2-oxo-3-quinazoline carboxylic acid-(endo-8-methyl-8-azabicyclo[3.2.1]oct-3-yl), ester Compound 27

Hydrochloride salt. M.p. >260° C.

Analysis $C_{18}H_{23}N_3O_3 \cdot HCl$: Found %: C 58.73; H 6.65; N 11.38. Calc. %: C 59.09; H 6.61; N 11.49.

1,4-dihydro-2(H)-2-oxo-3-quinazoline carboxylic acid-(1-methylpyrrolidin-3-yl), ester Compound 28

Hydrochloride salt (hygroscopic). M.p. 90°-91° C.

Analysis $C_{14}H_{17}N_3O_3 \cdot HCl$: Found %: C 52.90; H 6.18; N 13.24. Calc. %: C 53.93; H 5.82; N 13.48.

6-cyano-1,4-dihydro-2(H)-2-oxo-3-quinazoline carboxylic acid-(endo-8-methyl-8-azabicyclo[3.2.1]oct-3-yl), ester Compound 29

6-carbamoyl-1,4-dihydro-2(H)-2-oxo-3-quinazoline carboxylic acid-(endo-8-methyl-8-azabicyclo[3.2.1]oct-3-yl), ester Compound 30

M.p. 230°-232° C.

Analysis $C_{18}H_{22}N_4O_4$: Found %: C 59.83; H 6.23; N 15.51. Calc. %: C 60.32; H 6.19; N 15.63.

1,4-dihydro-7-fluoro-2(H)-2-oxo-3-quinazoline carboxylic acid-(endo-8-methyl-8-azabicyclo[3.2.1]oct-3-yl), ester Compound 31

Hydrochloride salt. M.p. >260° C.

Analysis $C_{17}H_{20}FN_3O_3 \cdot HCl$: Found %: C 54.76; H 5.79; N 11.29. Calc. %: C 55.21; H 5.72; N 11.36.

1,4-dihydro-2(H)-2-oxo-3-quinazoline carboxylic acid-(endo-8-benzyl-8-azabicyclo[3.2.1]oct-3-yl), ester Compound 32

Hydrochloride salt. M.p. 257°-258° C.

Analysis $C_{23}H_{25}N_3O_3 \cdot HCl$: Found %: C 64.62; H 6.18; N 9.71. Calc. %: C 64.56; H 6.12; N 9.82.

1,4-dihydro-2(H)-2-oxo-3-quinazoline carboxylic acid-(endo-8-ciclopropylmethyl-8-azabicyclo[3.2.1]oct-3-yl), ester Compound 33

M.p. 184°–186° C.
Analysis $C_{20}H_{25}N_3O_3$: Found %: C 67.46; H 7.15; N 11.75. Calc. %: C 67.58; H 7.09; N 11.82.

N-(endo-8-methyl-8-azabicyclo[3.2.1]oct-3-yl)-1,4-dihydro-2(H)-2,4-dioxo-3-quinazolinecarboxamide Compound 34

Hydrochloride salt. M.p. 184°–185° C. (dec.)
Analysis $C_{17}H_{20}N_4O_3.HCl$: Found %: C 55.07; H 5.82; N 15.18. Calc. %: C 55.97; H 5.80; N 15.36.

5-chloro-1,4-dihydro-2(H)-2-oxo-3-quinazoline carboxylic acid-(endo-8-methyl-8-azabicyclo[3.2.1]oct-3-yl), ester Compound 35

Hydrochloride salt. M.p. >260° C.
Analysis $C_{17}H_{20}ClN_3O_3.HCl$: Found %: C 52.67; H 5.47; N 10.83. Calc. %: C 52.86; H 5.48; N 10.88.

1,4-dihydro-5-methyl-2(H)-2-oxo-3-quinazoline carboxylic acid-(endo-8-methyl-8-azabicyclo[3.2.1]oct-3-yl), ester Compound 36

Hydrochloride salt. M.p. >260° C.
Analysis $C_{18}H_{23}N_3O_3.HCl$: Found %: C 58.53; H 6.67; N 11.38. Calc. %: C 59.09; H 6.61; N 11.49.

5,7-dichloro-1,4-dihydro-2(H)-2-oxo-3-quinazoline carboxylic acid-(endo-8-methyl-8-azabicyclo[3.2.1]oct-3-yl), ester Compound 37

1,4-dihydro-5-hydroxy-2(H)-2-oxo-3-quinazoline carboxylic acid-(endo-8-methyl-8-azabicyclo[3.2.1]oct-3-yl), ester Compound 38

Hydrochloride salt. M.p. >260° C.
Analysis $C_{17}H_{21}N_3O_4.HCl$: Found %: C 54.72; H 5.97; N 10.98. Calc. %: C 55.51; H 6.03; N 11.42.

1,4-dihydro-2(H)-2-oxo-3-quinazoline carboxylic acid-(endo-8-isopropyl-8-azabicyclo[3.2.1]oct-3-yl), ester Compound 39

Hydrochloride salt. M.p. 265°–266° C.
Analysis $C_{19}H_{25}N_3O_3.HCl$: Found %: C 59.90; H 6.97; N 10.98. Calc. %: C 60.07; H 6.90; N 11.06.

2,3,4,5-tetrahydro-2-oxo-1(H)-1,3-benzodiazepine-3-carboxylic acid-(endo-8-methyl-8-azabicyclo[3.2.1]oct-3-yl), ester Compound 40

M.p. 144°–145° C.
Analysis $C_{18}H_{23}N_3O_3$: Found %: C 65.33; H 7.09; N 12.67. Calc. %: C 65.63; H 7.04; N 12.76.

1,4-dihydro-2(H)-2-oxo-3-quinazoline carboxylic acid-(endo-8-ethyl-8-azabicyclo[3.2.1]oct-3-yl), ester Compound 41

Hydrochloride salt. M.p. >260° C.
Analysis $C_{18}H_{23}N_3O_3.HCl$: Found %: C 58.88; H 6.64; N 11.34. Calc. %: C 59.09; H 6.61; N 11.49.

EXAMPLE 16

1,2,3,4-tetrahydroquinoline-3-[(1-methylpiperidin-4-yl)carbonyl]-2-one

Compound 42

1,2,3,4-tetrahydroquinoline-2-one (1.87 g) was dissolved in dry THF (50 ml) and the solution was cooled to −70° C. n-Butyllithium (10.2 ml of a 2,5N solution in hexanes) was added dropwise under stirring at the same temperature, then the reaction mixture was allowed to come to −15° C. and was left at this temperature for 20 min. The reaction mixture was then cooled again to −70° C. and a solution of 1-methylpiperidin-4-carboxylic acid ethyl ester (2 g) in THF (5 ml) was added dropwise. The reaction mixture was allowed to come to room temperature and stirring was continued for 2 hrs. The reaction was quenched with water, acidified and washed with ethylacetate. The desired compound was extracted into ethylacetate after treatment with sodium carbonate. The compound (0.34 g) was crystallized from isopropyl ether/isopropanol.

M.p. 159°–161° C.
Analysis $C_{16}H_{20}N_2O_2$: Found %: C 70.54; H 7.40; N 10.26. Calc. %: C 70.56; H 7.40; N 10.28.
IR (nujol) ν (cm$^{-1}$): 3200, 1705, 1670, 1595.

Similarly the following compound was prepared:

1,2,3,4-tetrahydroquinoline-3-[(1-methylpiperidin-3-yl)carbonyl]-2-one

Compound 43

M.p. 170°–172° C.
Analysis $C_{16}H_{20}N_2O_2$: Found %: C 70.46; H 7.46; N 10.26. Calc. %: C 70.56; H 7.40; N 10.28.
IR (nujol) ν (cm$^{-1}$): 32,00, 1710, 1670, 1595.

Similarly, employing lithium diisopropilamide (LDA) and (endo-8-methyl-8-azabicyclo[3.2.1]oct-3-yl), chloroformate hydrochloride, the following compound was also obtained:

1,3,4,5-tetrahydro-2-oxo-2(H)-1-benzazepin-3-carboxylic-acid (endo-8-methyl-8-azabicyclo[3.2.1]oct-3-yl), ester Compound 44

Citric acid salt. M.p. 105°–110° C.
Analysis $C_{19}H_{24}N_2O_3.C_6H_8O_7$: Found %: C 57.14; H 6.31; N 5.19. Calc. %: C 57.69; H 6.20; N 5.38.

Similarly, employing sodium hydride in DMF, the following compounds were also obtained:

1,4-dihydro-2(H)-2,4-dioxo-3-quinazoline carboxylic acid-(endo-8-methyl-8-azabicyclo[3.2.1]oct-3-yl), ester Compound 45

M.p. 181°–183° C.
Analysis $C_{17}H_{19}N_3O_4$: Found %: C 61.73; H 5.89; N 12.56. Calc. %: C 62.04; H 5.81; N 12.76.
IR (nujol) (cm$^{-1}$): 1780, 1725, 1680

1,4-dihydro-2(H)-2-oxo-3-quinazoline carboxylic acid-(endo-8-methyl-8-azabicyclo[3.2.1]oct-3-yl), ester Compound 16

M.p. 175°–177° C.
Analysis $C_{17}H_{21}N_3O_3$: Found %: C 64.51; H 6.73; N 13.21. Calc. %: C 64.74; H 6.71; N 13.33.

1,4-dihydro-2(H)-2-oxo-3-quinazoline carboxylic acid-(1-azabicyclo[2.2.2]oct-3-yl), ester Compound 22

M.p. 152°-154° C.

Analysis $C_{16}H_{19}N_3O_3$: Found %: C 63.61; H 6.34; N 13.91. Calc. %: C 63.77; H 6.36; N 13.95.

EXAMPLE 17

1,4-dihydro-2(H)-2-oxo-3-quinazoline carboxylic acid-(endo-8-methyl-8-azabicyclo[3.2.1]oct-3-yl) ester, methobromide Compound 46

A solution of 1,4-dihydro-2(H)-2-oxo-3-quinazoline carboxylic acid-(endo-8-methyl-8-azabicyclo[3.2.1]oct-3-yl), ester (0.5 g) in acetone (15 ml) was dropped into a mixture of acetone (15 ml) and methylbromide (2M solution in diethylether, 15 ml) at 0° C. The reaction vessel was then closed and left aside at room temperature for 20 hrs. The raw material was obtained by evaporation of the solvent and was crystallized from ethanol. 0.3 g of the title compound were obtained. M.p. >260° C.

Analysis $C_{18}H_{24}BrN_3O_3$: Found %: C 52.44; H 5.87; N 10.14; Br 19.00. Calc. %: C 52.69; H 5.89; N 10.24; Br 19.47.

Similarly the following compounds were obtained:

1,4-dihydro-2(H)-2-oxo-3-quinazoline carboxylic acid-(endo-8-isopropyl-8-azabicyclo[3.2.1]oct-3-yl) ester, methobromide Compound 47

M.p. 259°-261° C.

Analysis $C_{20}H_{28}BrN_3O_3$: Found %: C 54.22; H 6.46; N 9.43. Calc. %: C 54.79; H 6.44; N 9.59.

1,4-dihydro-2(H)-2-oxo-3-quinazoline carboxylic acid-(endo-8-cyclopropylmethyl-8-azabicyclo[3.2.1]oct-3-yl) ester, methobromide Compound 48

M.p. 169°-172° C.

Analysis $C_{21}H_{28}BrN_3O_3$: Found %: C 55.23; H 6.28; N 9.19. Calc. %: C 56.00; H 6.27; N 9.33.

1,4-dihydro-2(H)-2-oxo-3-quinazoline carboxylic acid-(endo-8-methyl-8-azabicyclo[3.2.1]oct-3-yl) ester, cyclopropylmethobromide Compound 49

M.p. 257°-258° C.

Analysis $C_{21}H_{28}BrN_3O_3$: Found %: C 55.48; H 6.28; N 9.17. Calc. %: C 56.00; H 6.27; N 9.33.

1,4-dihydro-2(H)-2-oxo-3-quinazoline carboxylic acid-(endo-8-ethyl-8-azabicyclo[3.2.1]oct-3-yl) ester, methobromide Compound 50

M.p. 250°-252° C.

Analysis $C_{19}H_{26}BrN_3O_3$: Found %: C 53.19; H 6.22; N 9.63. Calc. %: C 53.78; H 6.18; N 9.90.

1,4-dihydro-2(H)-2-oxo-3-quinazoline carboxylic acid-(endo-8-methyl-8-azabicyclo[3.2.1]oct-3-yl) ester, ethobromide Compound 51

M.p. >260° C.

Analysis $C_{19}H_{26}BrN_3O_3$: Found %: C 53.73; H 6.23; N 9.76. Calc. %: C 53.78; H 6.18; N 9.90.

1,4-dihydro-2(H)-2-oxo-3-quinazoline carboxylic acid-(endo-8-benzyl-8-azabicyclo[3.2.1]oct-3-yl) ester, methobromide Compound 52

M.p. 212°-214° C.

Analysis $C_{24}H_{28}BrN_3O_3$: Found %: C 59.01; H 5.76; N 8.58. Calc. %: C 59.26; H 5.80; N 8.64.

EXAMPLE 18

1,4-dihydro-1-methyl-2(H)-2-oxo-3-quinazoline carboxylic acid-(endo-8-methyl-8-azabicyclo[3.2.1]oct-3-yl), ester Compound 53

Sodium hydride (0.048 g of an 80% dispersion in oil) was portionwise added at room temperature to a solution of 1,4-dihydro-2(H)-2-oxo-3-quinazoline carboxylic acid-(endo-8-methyl-8-azabicyclo[3.2.1]oct-3-yl), ester (0.5 g) in dry DMF. Once the gas evolution stopped, methyl iodide (0.1 ml) was added and the reaction mixture was stirred for 1 hour. Evaporation of the solvent left a residue which was taken up into water and methylene dichloride. From the organic layer a raw compound was obtained which was purified by flash chromatography (Silicagel, eluent: methylene dichloride/methanol/32% ammonium hydroxide 90:10:1).

0.12 g of the title compound were obtained. M.p. 110°-112° C.

Analysis $C_{18}H_{23}N_3O_3$: Found %: C 65.02; H 7.06; N 12.49. Calc. %: C 65.63; H 7.04; N 12.76.

EXAMPLE 19

1,4-dihydro-4-hydroxy-2(H)-2-oxo-3-quinazoline carboxylic acid-(endo-8-methyl-8-azabicyclo[3.2.1]oct-3-yl), ester Compound 54

A solution of 1,4-dihydro-2(H)-2-oxo-3-quinazoline carboxylic acid-(endo-8-methyl-8-azabicyclo[3.2.1]oct-3-yl) ester, hydrochloride (3.45 g) in water (100 ml) was brought to pH 7 by addition of saturated $Na_2CO_3$. While maintaining pH 7 by gradual addition of 0.1N sulphuric acid, a solution of potassium permanganate (3.1 g) in water (100 ml) was slowly added at the bottom of the reaction vessel. 81 ml of the $KMnO_4$ solution were added when disappearance of the starting material was detected by thin layer chromatography.

The reaction mixture was filtered, treated with 10% sodium hydroxide and extracted with ethyl acetate. After drying the organic phase left a residue which was crystallized from ethyl acetate. 1.55 g of the title compound were obtained. M.p. 178°-180° C.

Analysis $C_{17}H_{21}N_3O_4$: Found %: C 61.47; H 6.48; N 12.65. Calc. %: C 61.62; H 6.39; N 12.68.

Similarly the following compounds were obtained:

1.4-dihydro-7-fluoro-4-hydroxy-2(H)-2-oxo-3-quinazoline carboxylic
acid-(endo-8-methyl-8-azabicyclo[3.2.1]oct-3-yl), ester Compound 55

M.p. 169°–170° C.
Analysis $C_{17}H_{20}FN_3O_4$: Found %: C 58.03; H 5.81; N 11.84. Calc. %: C 58.45; H 5.77; N 12.03.

N-(endo-8-methyl-8-azabicyclo[3.2.1]oct-3-yl)-1,4-dihydro-4-hydroxy-2(H)-2-oxo-3-quinazoline carboxamide Compound 56

M.p. 150°–152° C.
Analysis $C_{17}H_{22}N_4O_3$: Found %: C 61.45; H 6.77; N 16.84. Calc. %: C 61.80; H 6.71; N 16.96.

EXAMPLE 20

1,4-dihydro-2(H)-2-oxo-3-quinazoline carboxylic acid-(endo-8-azabicyclo[3.2.1]oct-3-yl), ester Compound 57

A solution of 1,4-dihydro-2(H)-2-oxo-3-quinazoline carboxylic acid-(endo-8-benzyl-8-azabicyclo[3.2.1]oct-3-yl), ester hydrochloride (0.4 g) in ethanol (10 ml) was hydrogenated at room temperature and atmospheric pressure in the presence of 10% Pd/C (0.04 g). The usual work up afforded 0.25 g of the title compound. Hydrochloride salt. M.p. >260° C.
Analysis $C_{16}H_{19}N_3O_3 \cdot HCl$: Found %: C 55.81; H 6.04; N 12.24. Calc. %: C 56.89; H 5.97; N 12.44.

EXAMPLE 21

1,4-dihydro-2(H)-2-oxo-3-quinazoline carboxylic acid-(endo-8-amidino-8-azabicyclo[3.2.1]oct-3-yl), ester Compound 58

A mixture of 1,4-dihydro-2(H)-2-oxo-3-quinazoline carboxylic acid-(endo-8-azabicyclo[3.2.1]oct-3-yl) ester, hydrochloride (0.6 g), cyanamide (0.15 g) and water (0.07 g) was heated to 130°–140° C. until the fluid mass became a solid. The cooled reaction mixture was taken up in hot ethanol and the insoluble material discarded. The mother liquors were evaporated to dryness and the title compound (0.21 g) was obtained by flash chromatography technique (eluent: n-butanol/water/acetic acid 90:5:5).
Hydrochloride salt. M.p. 70°–75° C. (lyophilized).
Analysis $C_{17}H_{21}N_5O_3 \cdot HCl$: Found %: C 53.61; H 5.87; N 18.33; Cl 9.21. Calc. %: C 53.75; H 5.84; N 18.44; Cl 9.33.

EXAMPLE 22

1,4-dihydro-2(H)-2-oxo-3-quinazoline carboxylic acid-[endo-8-(iminomethyl)-8-azabicyclo[3.2.1]oct-3-yl], ester Compound 59

To a solution of 1,4-dihydro-2(H)-2-oxo-3-quinazoline carboxylic acid-(endo-8-azabicyclo[3.2.1]oct-3-yl), ester (0.5 g) in a mixture of methylene dichloride (5 ml) and ethanol (5 ml), ethyl formimidate hydrochloride (0.22 g) was added. The reaction mixture was stirred at room temperature for 2 hrs, then the solvents were removed. The pure title compound (0.13 g) was obtained by flash chromatography (eluent: isopropanol/water/acetic acid 80:10:10).
Hydrochloride salt. M.p. 70°–73° C. (lyophilized).
Analysis $C_{17}H_{20}N_4O_3 \cdot HCl$: Found %: C 55.13; H 5.91; N 15.07; Cl 9.51. Calc. %: C 55.97; H 5.80; N 15.36; Cl 9.72.

EXAMPLE 23

1,4-dihydro-2(H)-2-thioxo-3-quinazoline carboxylic acid-(endo-8-methyl-8-azabicyclo[3.2.1]oct-3-yl), ester Compound 60

A solution of N-(2-nitrobenzyl) (endo-8-methyl-8-azabicyclo[3.2.1]oct-3-yl)carbamate (2.0 g) and triethylamine (1.2 ml) in methylene dichloride (30 ml) was added dropwise and under stirring at room temperature to a solution of thiophosgene (0.6 ml) in the same solvent (10 ml). After ten minutes a solid separated. Stirring was continued for a further hour, then the solid was recovered by filtration. This solid was suspended in 1,2-dichlorobenzene (5 ml) and the suspension was heated to 160°–170° C. for 15 min. After cooling the solid is triturated with the same solvent and recovered by filtration. After crystallization in acetonitrile 0.28 g of pure title compound were obtained as the hydrochloride salt. M.p. 224°–225° C. (dec.).
Analysis $C_{17}H_{21}N_3O_2S \cdot HCl$: Found %: C 55.47; H 6.05; N 11.34; S 8.64. Calc. %: C 55.50; H 6.03; N 11.42; S 8.72.

EXAMPLE 24

1,4-dihydro-3(H)-2,1,3-benzothiadiazine-3-carboxylic acid-(endo-8-methyl-8-azabicyclo[3.2.1]oct-3-yl) ester, 2,2-dioxide Compound 62

Sulphunyl chloride (0.23 ml) in dry methylene dichloride (5 ml) was added dropwise to a solution of N-(2-nitrobenzyl) (endo-8-methyl-8-azabicyclo[3.2.1]oct-3-yl carbamate (1.0 g) and triethylamine (0.42 g) in the same solvent (15 ml) under stirring at room temperature. The reaction mixture darkened and separated some gummy material. After 30 min. stirring was stopped and the organic layer was concentrated to dryness. The residual was taken up into water and the pH of the solution was brought to 8.5 by adding saturated sodium bicarbonate. The raw title compound was extracted into ethylacetate; it was purified by flash chromatography on Silicagel (eluent methylene dichloride/methanol/32% NH$_4$OH 70:30:3). Evaporation of the eluent left 0.1 g of pure title compound. M.p. 155°–160° C.
Analysis $C_{16}H_{21}N_3O_4S$: Found %: C 54.27; H 6.04; N 11.54. Calc. %: C 54.68; H 6.02; N 11.96.

EXAMPLE 25

Endo-3-[(1,4-dihydro-2(H)-2-oxo-3-quinazolin-3-yl)carbonyloxyl-8-methyl-8-azabicyclo[3.2.1]octane, 8-oxide Compound 65

A mixture of 1,4-dihydro-2(H)-2-oxo-3-quinazoline carboxylic acid-(endo-8-methyl-8-azabicyclo[3.2.1]oct-3-yl)ester (2.7 g) and 35% hydrogen peroxide (2.5 g) in 75% EtOH (45 ml) was stirred at room temperature for 3 hours and then was left aside for 2 days. Sodium sulphite was added until no more peroxides were present then water was added and the resulting milky solution was washed with methylene dichloride. The aqueous phase was concentrated to dryness and the title compound was purified by flash chromatography over Silicagel (eluent: methylene dichloride/methanol/32% NH₄OH 80:20:2) and re-crystallized from acetone. 60 mg of pure title compound were afforded. M.p. 136°–140° C.

Analysis $C_{17}H_{21}N_3O_4.3H_2O$: Found %: C 53.11; H 6.98; N 10.90. Calc. %: C 52.98; H 7.06; N 10.90.

The following compounds can also be prepared:

1,4-dihydro-3(H)-2,1,3-benzothiadiazine-3-carboxylic acid-(endo-8-methyl-8-azabicyclo[3.2.1]oct-3-yl) ester, 2 oxide Compound 61

6-chloro-1,4-dihydro-3(H)-2,1,3-benzothiadiazine-3-carboxylic acid-(endo-8-methyl-8-azabicyclo[3.2.1]oct-3-yl) ester, 2-oxide Compound 63

6-chloro-1,4-dihydro-3(H)-2,1,3-benzothiadiazine-3-carboxylic acid-(endo-8-methyl-8-azabicyclo[3.2.1]oct-3-yl) ester, 2,2-dioxide Compound 64

According to the invention, the following not limitative examples of pharmaceutical compositions are reported:

EXAMPLE 26

Tablets active ingredient: 10 mg
lactose: 207 mg
corn starch: 30 mg
magnesium stearate: 3 mg.

Method of preparation: the active ingredient, lactose and corn starch were mixed and homogeneously moistened with water. After screening of the moist mass and drying in a tray drier, the mixture was again passed through a screen and magnesium stearate was added. Then the mixture was pressed into tablets weighing 250 mg each. Each tablet contains 10 mg of active ingredient.

EXAMPLE 27

Capsules active ingredient: 10 mg
lactose: 188 mg
magnesium stearate: 2 mg.

Method of preparation: the active ingredient was mixed with the auxiliary products, and the mixture was passed through a screen and mixed homogeneously in a suitable device. The resulting mixture was filled into hard gelatine capsules (200 ml per capsule); each capsule contains 10 mg of active ingredient.

EXAMPLE 28

Ampoules active ingredient: 2 mg
sodium chloride: 9 mg.

Method of preparation: the active ingredient and sodium chloride were dissolved in an appropriate amount of water for injection. The resulting solution was filtered and filled into vials under sterile conditions.

EXAMPLE 29

Suppositories active ingredient: 25 mg
semisynthetic gliderides of fatty acids: 1175 mg.

Method of preparation: the semisynthetic gliderides of fatty acids were melted and the active ingredient was added while stirring homogeneously. After cooling at a proper temperature the mass was poured into pre-formed moulds for suppositories weighing 1200 mg each. Each suppository contains 25 mg of active ingredient.

EXAMPLE 30

Oral drops active ingredient: 5 mg
sorbitol: 350 mg
propylene glycol: 200 mg
citric acid: 1 mg
sodium citrate: 3 mg
demineralized water: q.s. 1 ml.

Method of preparation: the active ingredient, citric acid and sodium citrate were dissolved in a mixture of a proper amount of water and propylene glycol. Then sorbitol was added and the final solution was filtered. The solution contains 1% of active ingredient and is administered by using a proper dropper.

What is claimed is:

1. A compound of the formula (I)

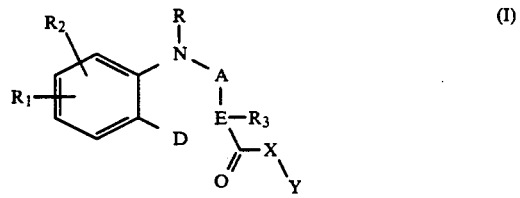

wherein

R represents H or $C_{1-6}$ alkyl;

$R_1$ and $R_2$ represent H, halogen, $C_{1-6}$ alkyl, $C_{1-6}$ alkoxy, $C_{1-6}$ alkylthio, $C_{1-6}$ alkoxycarbonyl, carboxyl, hydroxy, nitro, cyano, optionally $C_{1-4}$ alkyl mono- or disubstituted carbamoyl, optionally $C_{1-4}$ alkyl mono- or disubstituted amino, $C_{1-6}$ acylamino, $C_{1-4}$ alkoxy carbonylamino, $C_{1-6}$ alkylsulphynyl, $C_{1-6}$ alkylsulphonyl or $C_{1-6}$ acyl;

$R_3$ represents H, $C_{1-6}$ alkyl, aryl or aralkyl, or it may be absent;

A represents CO or C=S;

E represents nitrogen;

D represents CO or $CR_4R_5$ when the E—D bond is single, or D is C—R when the D—E bond is double, in which $R_4$ represents H, $C_{1-6}$ alkyl, aryl, aralkyl, hydroxy or $C_{1-4}$ alkoxy and $R_5$ represents H;

X represents oxygen or N—R, or it is absent;

Y represents a basic group selected from:

-continued

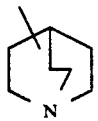

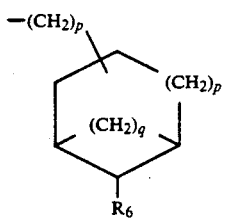

in which n is 2 or 3; p is 0 or 1 at the same time or not; q is 0,2 or 3; $R_6$ and $R_7$ may be at the same time or not H, $C_{1-4}$ alkyl, aralkyl or, when $R_7$ is H or $C_{1-4}$ alkyl, $R_6$ may be —$CR_8$=N—R in which $R_8$ represents H, $C_{1-4}$ alkyl or amino; or, a pharmaceutically acceptable acid addition salt or quaternary derivative thereof.

2. A compound of the formula (I) according to claim 1, further characterized in that Y represents endo-8-methyl-8-azabicyclo [3.2.1]oct-3-yl or endo-9-methyl-9-azabicyclo[3.2.1]oct-3-yl, E is nitrogen, R is hydrogen, $R_3$ is absent, the E—D bond is single and $R_1$, $R_2$, D and X are as defined in claim 1, or a pharmaceutically acceptable acid addition salt thereof.

3. In accordance with claim 1, a compound of formula I selected from:

1,4-dihydro-2(H)-2-oxo-3-quinazoline carboxylic acid-(endo-8-methyl-8-azabicyclo[3.2.1]oct-3-yl, ester;

N-(endo-8-methyl-8-azabicyclo[3.2.1]oct-3-yl)-1,4-dihydro-2(H)-2-oxo-quinazoline-3-carboxamide;

7-chloro-1,4-dihydro-2(H)-2-oxo-3-quinazoline carboxylic acid-(endo-8-methyl-8-azabicyclo[3.2.1]oct-3-yl), ester;

1,4-dihydro-6-fluoro-2(H)-2-oxo-3-quinazoline carboxylic acid-(endo-8-methyl-8-azabicyclo[3.2.1]oct-3-yl), ester;

1,4-dihydro-4-hydroxy-2(H)-2-oxo-3-quinazoline carboxylic acid-(endo-8-methyl-8-azabicyclo[3.2.1]oct-3-yl, ester;

and pharmaceutically acceptable acid addition salts thereof.

4. A method for treating a warm-blooded animal suffering from an obstructive acute or a chronic spastic disorder of the respiratory tract, which method comprises administering to such host a therapeutically effective amount of a compound of formula I, as set forth in claims 1, 2 or 3.

5. The method of claim 4, wherein the disorder to be treated is bronchoconstriction, chronic bronchitis, emphysema or asthma.

6. A pharmaceutical composition suitable for the treatment of obstructive acute or chronic spastic disorders of the respiratory tract, comprising a therapeutically effective amount of a compound of formula I, as set forth in claims 1, 2 or 3, and a pharmaceutically acceptable carrier.

* * * * *

UNITED STATES PATENT AND TRADEMARK OFFICE
CERTIFICATE OF CORRECTION

PATENT NO. : 5,106,851

DATED : April 21, 1992

INVENTOR(S) : Turconi et al.

It is certified that error appears in the above-identified patent and that said Letters Patent is hereby corrected as shown below:

In the abstract, formula I, that portion of the formula reading D-----E should read D̲-̲-̲-̲-̲-̲E.

In column 4, line 23, B-D should read E-D.

In column 8, line 42, and in column 10, line 19, the reference to compound 49 should be a reference to compound 54.

In column 28, formula I, that portion of the formula which includes D and E should read D̲-̲-̲-̲-̲-̲E.

Signed and Sealed this

Twenty-first Day of September, 1993

Attest:

BRUCE LEHMAN

Attesting Officer     Commissioner of Patents and Trademarks